US005485349A

United States Patent [19]
Kelly et al.

[11] Patent Number: 5,485,349
[45] Date of Patent: Jan. 16, 1996

[54] HEAT-DISSIPATING ELECTRONIC APPARATUS FOR USE AT A PATIENT'S BEDSIDE

[75] Inventors: Cliff Kelly, Windham, N.H.; Helen C. Crouse, Waltham; Per Hoel, Magnolia, both of Mass.

[73] Assignee: Siemens Medical Systems, Inc., Iselin, N.J.

[21] Appl. No.: 253,643

[22] Filed: Jun. 3, 1994

[51] Int. Cl.⁶ .................................................. H05H 7/20
[52] U.S. Cl. ........................ 361/690; 361/715; 361/730; 361/752
[58] Field of Search ................................. 165/80.3, 185; 361/600, 679, 688, 689, 690, 704, 707, 709–711, 715–716, 728, 730, 735, 737, 744, 752

[56] References Cited

U.S. PATENT DOCUMENTS

| 3,940,665 | 2/1976 | Seki | 361/688 |
| 4,241,380 | 12/1980 | Lehmann et al. | 361/690 |
| 5,218,516 | 6/1993 | Cullins et al. | 361/690 |

FOREIGN PATENT DOCUMENTS 4266091  9/1992  Japan ..................................... 361/697

Primary Examiner—Gregory D. Thompson
Attorney, Agent, or Firm—Lawrence C. Edelman

[57] ABSTRACT

The control unit of an automatic blood pressure monitor has a central chimney-shaped heat sink which is open at the top and the bottom. Air rising through the chimney dissipates heat generated during operation of the device. Additionally, in the event that liquid is accidently spilled from e.g. a bag of saline solution, it is directed downwardly through the chimney via a funnel.

4 Claims, 2 Drawing Sheets

5,485,349

HEAT-DISSIPATING ELECTRONIC APPARATUS FOR USE AT A PATIENT'S BEDSIDE

BACKGROUND OF THE INVENTION

The invention relates to electronic apparatus, and more particularly relates to electronic apparatus for medical applications. In its most immediate sense, the invention relates to electronic medical apparatus for use at a patient's bedside.

It is known to mount electrical apparatus at a patient's bedside for, e.g., monitoring a patient's blood pressure, electrocardiogram, etc.

Occasionally, such apparatus generates substantial heat, which must be dissipated to prevent overheating. Conventionally, such dissipation is carried out by using a conventional heat sink, which exposes externally-extending fins to the outside air.

This has the disadvantage of presenting an unattractive appearance. Additionally, because of limitations on the surface area available for thermal connection of the electronic components, this places inconvenient constraints on the mechanical packaging of the apparatus.

In accordance with the invention, the apparatus is provided with a chimney-shaped heat sink having sides and an open top and bottom. The electronic heat-generating components are thermally connected to at least one of the sides, and a housing surrounds the components and the sides of the heat sink while leaving the top and bottom of the heat sink open to permit air to rise up through it. By using such a structure, more surface area is available for thermal attachment of electronic components and it is possible to manufacture a more attractive device.

Advantageously, the housing is funnel-shaped at the top of the heat sink; this directs liquids through the heat sink and prevents liquid from potentially shorting out the internal circuitry.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
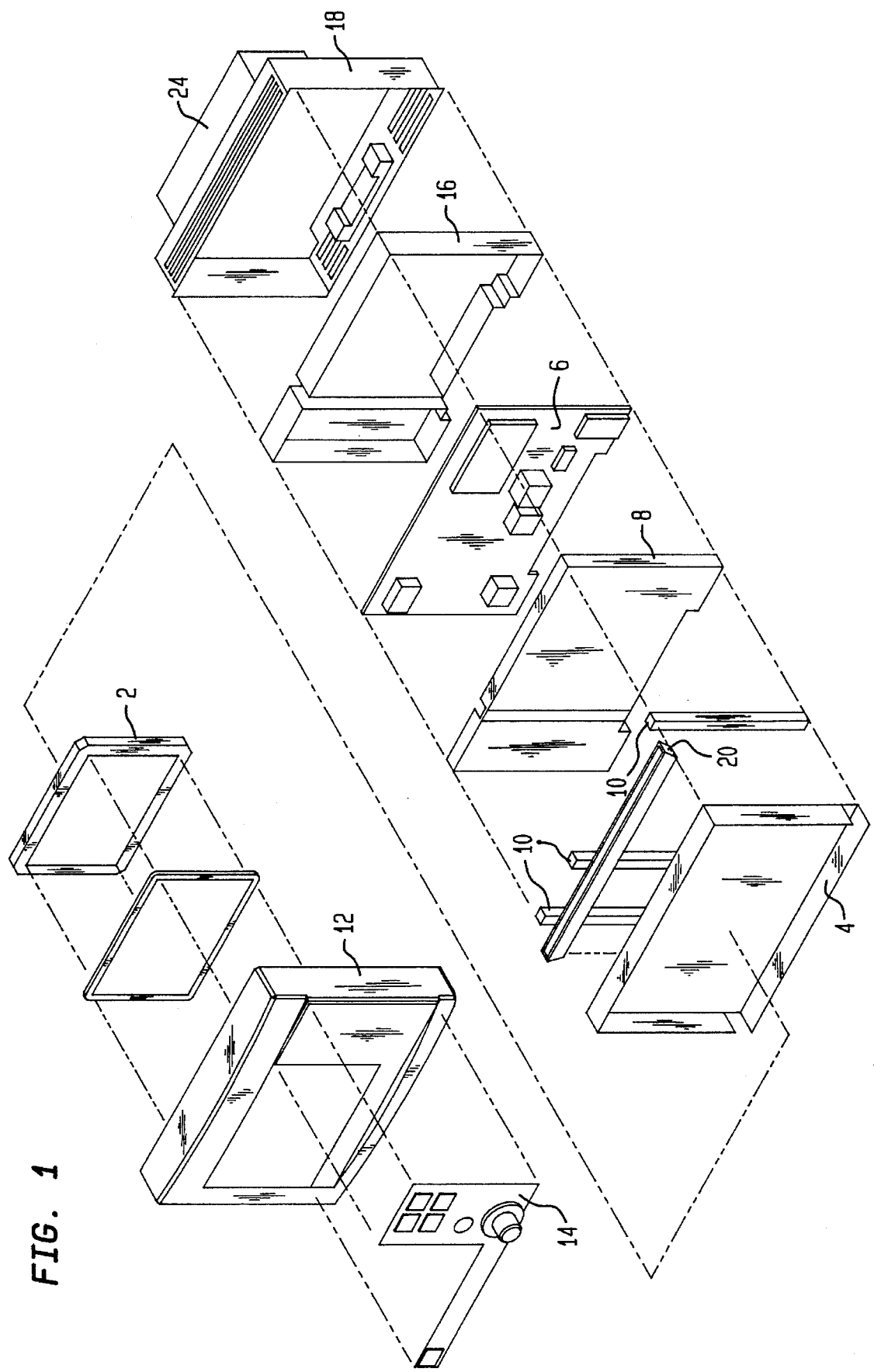
FIG. 1 shows an exploded view of a preferred embodiment of the invention.
Figure 2:
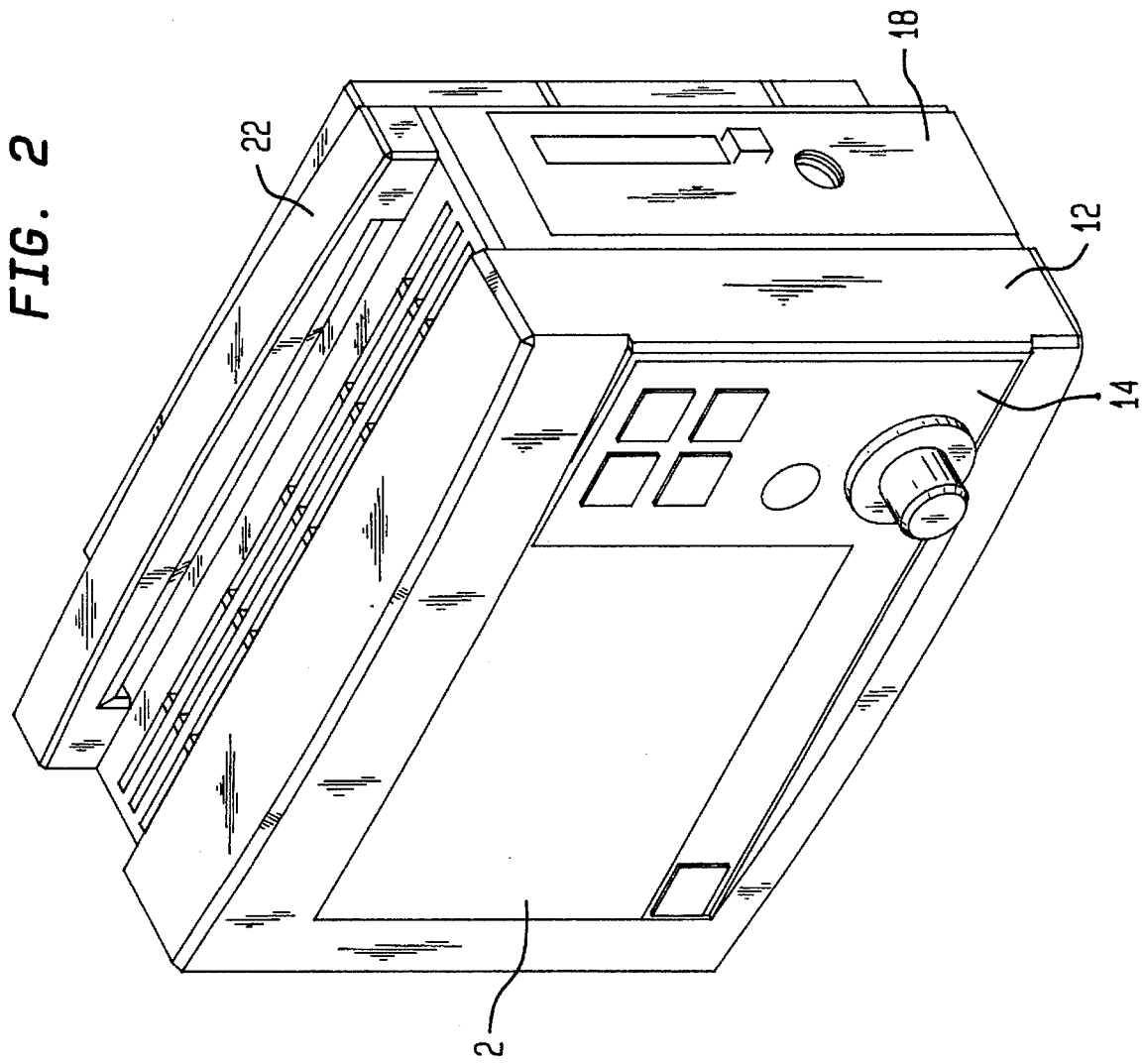
FIG. 2 shows a perspective view of a preferred embodiment of the invention.

The following description relates to an automatic blood pressure monitor, but this is not a part of the invention. The drawings are not to scale, and many details have been omitted in the interest of clarity.

In an automatic blood pressure monitor control unit, a liquid crystal display 2 is mounted to a shell half 4 (of a thermally conductive material such as aluminum) and thermally connected therewith using a thermally conductive material (not shown) manufactured under the CHOMERICS trademark. A printed circuit board 6 is mounted to another shell half 8 (likewise made of e.g. aluminum) and is likewise thermally connected therewith. The shell halves 4 and 8 are spaced apart by foam spacers 10. A rear shield 16 mates with the shell half 8 in such a manner as to enclose the printed circuit board 6.

A front housing half 12 contains a control panel 14 which is used to operate the electrical elements within the control unit. A rear housing half 18 mates with the front housing half 12 and thereby encloses the shell halves 4 and 8, the printed circuit board 6 and the rear shield 16. A central chimney is defined by the shell halves 4 and 8 (which are spaced apart by the spacers 10); the chimney has an open top and an open bottom. A funnel 20, located at the top of the housing, communicates with the open top of the chimney.

A handle 22 is mounted to the rear housing half 18. When the device is to be lifted, the handle 22 can be lifted upward for a short distance; this allows the user's fingers to fit beneath the handle 22 without being pinched. A battery 24 may be detachably secured to the rear of the rear housing half 18 to provide power to the device.

In use, the liquid crystal display 2 and the printed circuit board 6 generate heat. This heat is transferred to the shell halves 4 and 8, which transfer it to air (not shown) which enters the chimney at the open bottom and leaves it at the open top.

If liquid, e.g. saline solution, is spilled on the top of the assembled device, the liquid is directed into the chimney by the funnel 20. The liquid then flows downwardly through the chimney and out the bottom.

Although a preferred embodiment has been described above, the scope of the invention is limited only by the following claims:

We claim:

1. An electronic apparatus designed for use at a patient's bedside, comprising:

a chimney-shaped heat sink having sides and open top and bottom ends;

electronic components thermally connected to at least one side of the heat sink;

a generally rectangular housing having a top, a bottom and sides surrounding and enclosing the components and the sides of the heat sink, the housing having openings in said top and said bottom, said openings mating with the top and bottom ends of the heat sink; and a funnel positioned in an abutting manner between the open top end of said heat sink and the top of said housing so that said funnel directs the passage of fluids accidentally spilled on the top of said housing, through the open top and bottom ends of said heat sink and out of the bottom of said housing via the mating openings in said housing.

2. The apparatus of claim 1, wherein the apparatus is an automatic blood pressure monitor.

3. The apparatus of claim 1, wherein said housing and said heat sink each comprise left and right halves, the left and right halves of said heat sink being positioned in the left and right halves of said housing, respectively; and means positioned between said heat sink halves and extending between the open top and bottom ends thereof so as to define the dimensions of a chimney-shaped flow path between the open top and bottom ends of said heat sink.

4. The apparatus of claim 3, wherein said means cooperates with said funnel so that any fluids accidentally spilled on the top of said housing remain within said chimney-shaped flow path.

* * * * *